(12) United States Patent
Brothers et al.

(10) Patent No.: US 12,029,706 B2
(45) Date of Patent: Jul. 9, 2024

(54) METHODS FOR TREATING MUCOPOLYSACCHARIDOSIS

(71) Applicant: UNIVERSITY OF MIAMI, Miami, FL (US)

(72) Inventors: Shaun Brothers, Miami, FL (US); Claes Wahlestedt, Miami, FL (US); Claude Henry Volmar, Miami, FL (US)

(73) Assignee: University of Miami, Miami, FL (US)

( * ) Notice: Subject to any disclaimer, the term of this patent is extended or adjusted under 35 U.S.C. 154(b) by 242 days.

(21) Appl. No.: 17/021,185

(22) Filed: Sep. 15, 2020

(65) Prior Publication Data
US 2021/0008005 A1    Jan. 14, 2021

Related U.S. Application Data

(63) Continuation of application No. 15/742,779, filed as application No. PCT/US2016/041564 on Jul. 8, 2016, now abandoned.
(Continued)

(51) Int. Cl.
| | |
|---|---|
| *A61K 31/05* | (2006.01) |
| *A61K 9/00* | (2006.01) |
| *A61K 31/03* | (2006.01) |
| *A61K 31/09* | (2006.01) |
| *A61K 31/166* | (2006.01) |
| *A61K 31/185* | (2006.01) |
| *A61K 31/194* | (2006.01) |
| *A61K 31/235* | (2006.01) |

(Continued)

(52) U.S. Cl.
CPC ............ *A61K 31/05* (2013.01); *A61K 9/0019* (2013.01); *A61K 9/0053* (2013.01); *A61K 31/03* (2013.01); *A61K 31/09* (2013.01); *A61K 31/166* (2013.01); *A61K 31/185* (2013.01); *A61K 31/194* (2013.01); *A61K 31/235* (2013.01); *A61K 31/36* (2013.01); *A61K 31/423* (2013.01); *A61K 31/69* (2013.01); *A61K 31/7004* (2013.01); *A61K 45/06* (2013.01); *A61P 3/00* (2018.01)

(58) Field of Classification Search
CPC ........................................................ A61P 3/00
See application file for complete search history.

(56) References Cited

U.S. PATENT DOCUMENTS

| | | |
|---|---|---|
| 8,350,093 B2 | 1/2013 | DiMauro |
| 2007/0249647 A1 | 10/2007 | Vander Jagt et al. |

(Continued)

FOREIGN PATENT DOCUMENTS

| | | |
|---|---|---|
| WO | WO-2009012551 A1 | 1/2009 |
| WO | WO-2009012910 A1 | 1/2009 |

(Continued)

OTHER PUBLICATIONS

Rius et al. "Trans- but not Cis-Resveratrol impairs Angiotensin-II-Mediated Vascular Inflammation through Inhibition of NF-κB Activation and Peroxisome Proliferator-Activated Receptor-γ Upregulation", The Journal of Immunology, 2010, vol. 185, issue 6, pp. 3718-3727.

(Continued)

*Primary Examiner* — Clinton A Brooks
*Assistant Examiner* — Andrew P Lee
(74) *Attorney, Agent, or Firm* — Merchant & Gould, P.C.

(57) ABSTRACT

The present invention provides methods and compositions for the treatment of mucopolysaccharidoses (MPS).

13 Claims, 3 Drawing Sheets

Related U.S. Application Data

(60) Provisional application No. 62/190,935, filed on Jul. 10, 2015.

(51) Int. Cl.

| | | |
|---|---|---|
| *A61K 31/36* | (2006.01) |
| *A61K 31/423* | (2006.01) |
| *A61K 31/69* | (2006.01) |
| *A61K 31/7004* | (2006.01) |
| *A61K 45/06* | (2006.01) |
| *A61P 3/00* | (2006.01) |

(56) References Cited

U.S. PATENT DOCUMENTS

| | | |
|---|---|---|
| 2009/0326000 A1 | 12/2009 | Hull et al. |
| 2010/0048577 A1 | 2/2010 | Leheste et al. |
| 2010/0183524 A1 | 7/2010 | Zielinski et al. |
| 2010/0310615 A1 | 12/2010 | Vercauteren |
| 2011/0189275 A1 | 8/2011 | Schultheiss et al. |
| 2012/0058088 A1 | 3/2012 | Sardi |
| 2012/0149663 A1 | 6/2012 | Brown et al. |
| 2012/0165280 A1 | 6/2012 | Mayeux et al. |
| 2012/0178801 A1 | 7/2012 | Majeed |
| 2013/0035305 A1 | 2/2013 | Heger et al. |
| 2013/0040921 A1 | 2/2013 | Rodriguez et al. |
| 2013/0310615 A1 | 11/2013 | Ohler et al. |

FOREIGN PATENT DOCUMENTS

| | | |
|---|---|---|
| WO | WO-2009032870 A2 | 3/2009 |
| WO | WO-2009061787 A1 | 5/2009 |
| WO | WO-2010004256 A1 | 1/2010 |
| WO | WO-2011073482 A1 | 6/2011 |
| WO | WO-2011130400 A1 | 10/2011 |
| WO | WO-2012112670 A1 | 8/2012 |
| WO | WO-2012129499 A1 | 9/2012 |
| WO | WO-2012154956 A2 | 11/2012 |
| WO | WO-2012156275 A1 | 11/2012 |
| WO | WO-2014172776 A1 | 10/2014 |
| WO | WO-2015097088 A1 | 7/2015 |

OTHER PUBLICATIONS

Berge et al., "Pharmaceutical Salts," *J. Pharm. Sciences*, 66(1):1-19 (1977).

International Preliminary Report on Patentability Chapter I, for International Application No. PCT/US2016/041564, dated Jan. 16, 2018.

International Search Report and Written Opinion of the International Searching Authority, for International Application No. PCT/US2016/041564, dated Sep. 22, 2016.

Pezzuto et al., "Resveratrol derivatives: a patent review (2009-2012)," *Expert Opin. on Ther. Patents*, 23(12):1529-1546 (2013).

Roupe et al., "Pharmacokinetics of selected stilbenes: rhapontigenin, piceatannol and pinosylvin in rats," *J. Pharm. Pharmacol.*, 58(11):1443-50 (2006).

Setoguchi et al., "Absorption and Metabolism of Piceatannol in Rats," *J. Agric. Food Chem.*, 62(12):2541-8 (2014).

Stahl et al., *The Handbook of Pharmaceutical Salts, Properties, Selection, and Use*, P. H. Stahl and C. G. Wermuth (eds.), Verlag Helvetica Chimica Acta, Zurich (Switzerland) 2002.

Bhakhtiarova et al., "Resveratrol inhibits firefly luciferase", Biochemical and Biophysical Research Communications, 351 (2006) 481-484.

METHODS FOR TREATING MUCOPOLYSACCHARIDOSIS

CROSS-REFERENCE TO RELATED APPLICATION

This application is a continuation of U.S. application Ser. No. 15/742,779, filed Jan. 8, 2018, now abandoned, which is a National Stage Application of International Patent Application No. PCT/US2016/041564, filed Jul. 8, 2016, and which claims the priority benefit of U.S. Provisional Patent Application No. 62/190,935, filed Jul. 10, 2015, the disclosures of which are incorporated herein by reference in their entireties.

FIELD OF THE INVENTION

The present invention relates to compositions and methods for treating mucopolysaccharidosis (MPS).

BACKGROUND

Mucopolysaccharidosis (MPS) constitutes a class of lysosomal storage disorders characterized by the excessive accumulation of glycosaminoglycans (GAGs) within the lysosomes of various tissues. MPS patients either do not produce enough of the enzymes required to degrade GAGs or produce defective enzymes that do not function properly. As a result, undegraded or partially degraded GAGs accumulate and interfere with the normal function of cells, tissues, and organs, and affect the normal growth and development of individuals. Clinical features vary in severity and include organomegaly, skeletal dysplasia, cardiac and pulmonary obstruction, and neurological deterioration.

There are seven distinct clinical types of MPS with numerous subtypes. MPS is an inherited disorder, and a myriad of genetic mutations have been identified for each of the MPS disorders. For example, mucopolysaccharidosis I (MPS I) is an autosomal recessive disorder caused by a loss of the enzyme α-L-iduronidase (IDUA). MPS I is further subdivided into three subtypes: Scheie (MPS I-S), a mild form; Hurler/Scheie (MPS I-H/S), an intermediate form; and Hurler (MPS I-H), the most severe form. Hurler syndrome is characterized by a near total absence of α-L-iduronidase activity, resulting in heart and liver diseases and mental deterioration as well as death in childhood. Currently, the only available treatment of MPS is enzyme replacement therapy, although this treatment is very expensive and therefore not available for many afflicted with an MPS condition.

Accordingly, there remains an urgent need for alternative and/or less costly pharmacological therapies for the treatment of MPS.

SUMMARY OF THE INVENTION

The present invention provides compositions and methods for treating mucopolysaccharidosis (MPS). The methods of the invention comprise administering to a subject in need thereof a therapeutically effective amount of a stilbene or stilbenoid compound, such as one or more hydroxylated or carboxylated stilbenoids, such as resveratrol, piceatannol, or 4,4'-stilbenedicarboxylic acid. In various embodiments, the invention provides methods for treating MPS I-H, MPS I-S, MPS I-H/S, MPS II, MPS III A, MPS III B, MPS III C, MPS III D, MPS IV A, MPS IV B, MPS VI, MPS VII, or MPS IX, particularly where the subject's disorder is not characterized by a complete lack of enzyme activity. As shown herein, stilbenoid compounds have the effect of increasing IDUA activity, which may in-part be due to an increase in enzyme expression. In some embodiments, the stilbene or stilbenoid compound is capable of crossing the blood-brain barrier, providing additional advantages in addressing the neurological manifestations of MPS.

In various embodiments, the stilbene or stilbenoid compound is formulated as a pharmaceutical composition for oral administration. Alternatively, the pharmaceutical composition may be formulated for parenteral administration. In some embodiments, the pharmaceutically composition may be administered to the subject at least once daily. A therapeutically effective amount of the pharmaceutical composition is from about 10 mg to about 5000 mg daily in some embodiments.

Other aspects and embodiments of the invention will be apparent from the following detailed description.

DETAILED DESCRIPTION

Figure 1:
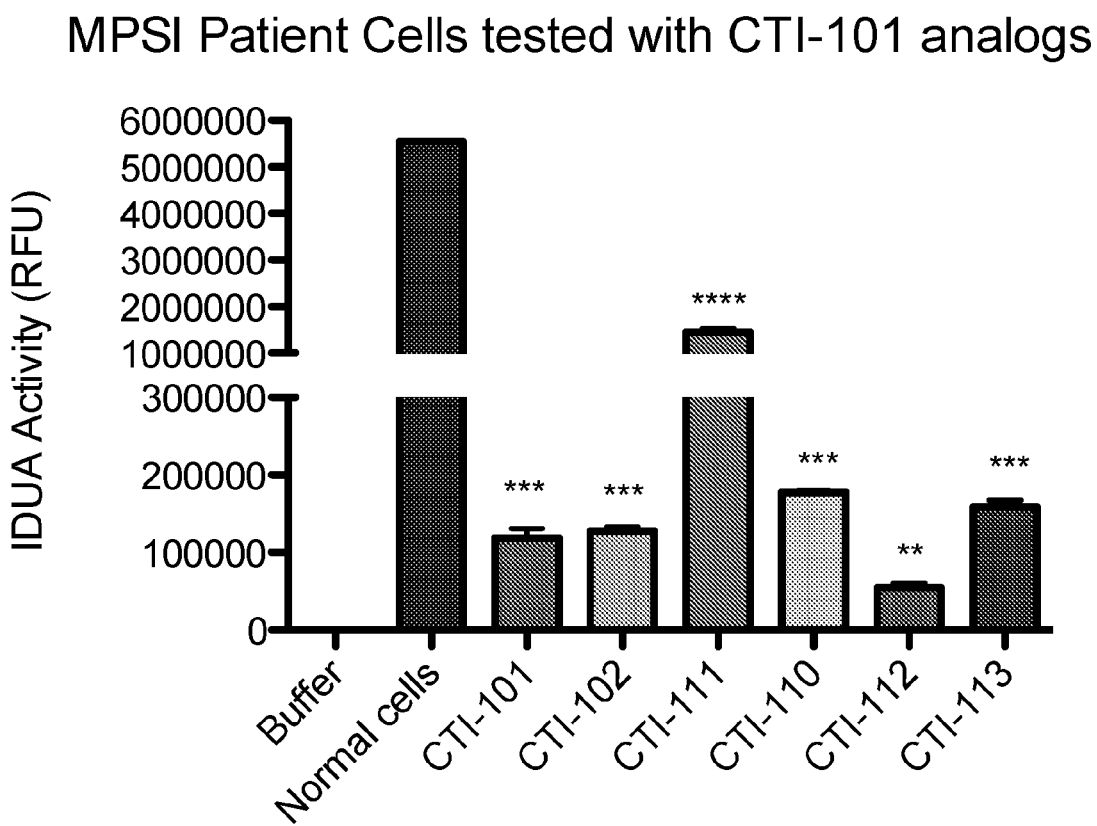
FIG. 1 shows that treatment of MPS I patient cells with resveratrol and various stilbenoid compounds resulted in an increase in IDUA activity. CTI-101 is piceatannol, CTI-102 is resveratrol, CTI-111 is 4,4'-stilbenedicarboxylic acid.

The present invention provides compositions and methods for treating mucopolysaccharidosis (MPS). Table 1 below describes the different types of MPS that may be treated using compositions and methods of the invention.

TABLE 1

MUCOPOLYSACCHARIDOSIS

| Type | Name of Syndrome | Deficient Enzyme |
|---|---|---|
| MPS I-H | Hurler syndrome | α-L-iduronidase |
| MPS I-S | Scheie syndrome | α-L-iduronidase |
| MPS I-H/S | Hurler-Scheie syndrome | α-L-iduronidase |
| MPS II | Hunter syndrome | Iduronate sulfatase |
| MPS III A | Sanfilippo syndrome type A | Heparan-N-sulfatase |
| MPS III B | Sanfilippo syndrome type B | α-N-acetylglucosaminidase |
| MPS III C | Sanfilippo syndrome type C | Acetyl-CoA-glucosaminide-acetyltransferase |
| MPS III D | Sanfilippo syndrome type D | N-acetyl-glucosamine-6-sulfatase |
| MPS IV A | Morquio syndrome type A | N-acetyl-galactosamine-6-sulfatase |
| MPS IV B | Morquio syndrome type B | β-galactosidase |
| MPS VI | Maroteaux-Lamy syndrome | N-acetylgalactosamine-4-sulfatase |
| MPS VII | Sly syndrome | β-glucuronidase |
| MPS IX | Natowicz syndrome | Hyaluronidase |

A subject with MPS may be diagnosed by a urine test to determine the levels of GAGs. MPS patients usually will have abnormally high levels of GAGs in the urine. Additionally, diagnosis may be made through tests which measure the enzymatic activities of various enzymes that are required for GAG degradation as listed in Table 1. In normal individuals, the tests may show white blood cells, serum, and skin cells that contain normal enzyme activity. In MPS patients, the enzyme activity may be much lower or absent. In addition, genetic tests may be carried out to detect specific genetic mutations associated with defective enzyme.

In various embodiments, the compositions and methods of the invention are effective in treating MPS by restoring the expression and/or the enzymatic activity of the enzymes involved in the degradation of glycosaminoglycans (GAGs). In an embodiment, the compositions and methods of the invention restore the expression and/or the enzymatic activity of α-L-iduronidase. In an embodiment, the compositions and methods of the invention restore the expression and/or the enzymatic activity of iduronate sulfatase. In an embodiment, the compositions and methods of the invention restore the expression and/or the enzymatic activity of heparan-N-sulfatase. In an embodiment, the compositions and methods of the invention restore the expression and/or the enzymatic activity of α-N-acetylglucosaminidase. In an embodiment, the compositions and methods of the invention restore the expression and/or the enzymatic activity of acetyl-CoA-glucosaminide-acetyltransferase. In an embodiment, the compositions and methods of the invention restore the expression and/or the enzymatic activity of N-acetyl-glucosamine-6-sulfatase. In an embodiment, the compositions and methods of the invention restore the expression and/or the enzymatic activity of N-acetyl-galactosamine-6-sulfatase. In an embodiment, the compositions and methods of the invention restore the expression and/or the enzymatic activity of N-acetyl-galactosamine-6-sulfatase. In an embodiment, the compositions and methods of the invention restore the expression and/or the enzymatic activity of β-galactosidase. In an embodiment, the compositions and methods of the invention restore the expression and/or the enzymatic activity of N-acetylgalactosamine-4-sulfatase. In an embodiment, the compositions and methods of the invention restore the expression and/or the enzymatic activity of β-glucuronidase. In an embodiment, the compositions and methods of the invention restore the expression and/or the enzymatic activity of hyaluronidase.

In some embodiments, the compositions and methods of the invention are effective in treating the neurological symptoms of MPS. For example, treated subjects may experience improvements in intellect and behavior. In another example, compositions and methods of the invention may slow down or stop the progression of mental decline in MPS subjects. In some embodiments, the compositions and methods of the invention are effective in treating the skeletal abnormalities of MPS. For example, compositions and methods of the invention may effective treat the joint and spinal cord problems of MPS subjects. In some embodiments, the compositions and methods of the invention are effective in treating the liver and/or spleen enlargement of MPS subjects.

Compositions and methods of the invention contemplate the use of stilbene or stilbenoid compounds for treatment of MPS. Exemplary stilbenoid compounds include stilbene scaffolds having from one to ten modifications (e.g., from one to five or from one to four substituents), which in some embodiments may be independently selected from hydroxyl, alkyl, alkenyl, carboxyl, alkyloxy, amino, amido, aryl, halogen or other substituent disclosed herein. The compositions and methods contemplate pharmaceutically acceptable salts, esters, or prodrugs of stilbene and stilbenoid compounds described herein. In these or other embodiments, the stilbenoid comprises one or more carbocyclic or heterocyclic substituents. The stilbenoid in various embodiments is a hydroxylated stilbene with from one to four hydroxylations.

In some embodiments, the stilbenoid is a dicarboxylic acid derivative of stilbene. In some embodiments, the stilbenoid comprises one, two, or three stilbene scaffolds, which may be linked by linear, branched, or cyclic hydrocarbon groups, and which may contain one, two, or three heteroatoms. Exemplary stilbenoid compounds are provided herein. The stilbene or stilbenoid may be cis- or trans-configuration. In certain embodiments, the compound is a trans-stilbenoid.

The term "pharmaceutically acceptable salt" as used herein refers to those salts which are suitable for use when in contact with the tissues of humans and other animals without undue toxicity, irritation, allergic response and the like, and have the desired pharmacological properties. Pharmaceutically acceptable salts are well known in the art and can include those listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, the entire contents of which are hereby incorporated by reference.

The term "pharmaceutically acceptable ester" as used herein refers to those esters which are suitable for use in contact with the tissues of humans and other animals without undue toxicity, irritation, allergic response and the like, and have the desired pharmacological properties. Pharmaceutically acceptable esters are well known in the art. Exemplary pharmaceutically acceptable esters include, but are not limited to, esters formed from carboxy, sulfonyloxy, and phosphonoxy groups present in a compound.

Substituents as identified herein may be independently selected from any suitable substituent. Generally, suitable substituents include, but are not limited to acyl, acyloxy, alkyl, heteroalkyl, alkenyl, heteroalkenyl, alkynyl, heteroalkynyl, alkoxy, alkoxycarbonyl, cycloalkyl, heterocycloalkyl, aryl, arylalkyl, heteroaryl, heteroarylalkyl, hydroxy, halo, cyano, trifluoromethyl, trifluoromethoxy, nitro, and trimethylsilanyl. Exemplary substituents include those independently selected from ethers, esters, sulfides, disulfides, sulfonyl, sulfinyl, sulfonamidyl, sulfonate, sulfoxyl, phosphate esters, phosphines, borate esters, halogens, carbonyl, carboxylate, carbamate, amines, imides, and quanidines. For example, exemplary substituents include Cl, F, Br, —OR$^b$, —SR$^b$, —OC(O)—R$^b$, —N(R$^b$)2, —C(O)R$^b$, —C(O)OR$^b$, —OC(O)N(R$^b$)2, —C(O)N(R$^b$)2, —N(R$^b$)C(O)OR$^b$, —N(R$^b$)C(O)R$^b$, —N(R$^b$)C(O)N(R$^b$)2, N(R$^b$)C(NR$^b$)N(R$^b$)2, —N(R$^b$)S(O)$_2$R$^b$, —S(O)OR$_b$, —S(O)$_2$OR$^b$, —S(O)OR$^b$)$_2$, —S(O)$_2$N(R$^b$)$_2$, or PO$_3$(R$^b$)$_2$ where each R$^b$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl.

Alkyl substituents may be straight or branched, and may be substituted or unsubstituted (e.g., haloalkyl). In some embodiments, the alkyl group may have from 1 to 12 carbon atoms, e.g. 1 carbon atom, 2 carbon atoms, 3 carbon atoms, 4 carbon atoms etc., up to and including about 12 carbon atoms. Exemplary alkyl groups include methyl, ethyl, propyl, isopropyl, n-butyl, iso-butyl, sec-butyl isobutyl, tertiary butyl, pentyl, isopentyl, neopentyl, hexyl, septyl, octyl, nonyl and decyl. The alkyl substituent may be attached to the rest of the molecule by a single bond.

Alkenyl substituents may be straight or branched, and may be substituted or unsubstituted. In some embodiments, the alkenyl group may contain from 2 carbon atoms to about 12 carbon atoms, e.g., the alkenyl group may consist of 2 carbon atoms, 3 carbon atoms, 4 carbon atoms etc., up to and including about 12 carbon atoms. The alkenyl substituent may be attached to the rest of the molecule by a single bond or by a double bond.

Alkynyl substituents may be straight or branched, and may be substituted or unsubstituted. In some embodiments, the alkynyl group contains from 2 to about 12 carbon atoms (e.g., 2, 3, or 4 carbon atoms). The alkynyl may be attached to the rest of the molecule by a single bond, for example, ethynyl, propynyl, butynyl, pentynyl and hexynyl.

Cycloalkyl substituents may be monocyclic or polycyclic substituents, which may be saturated, or partially unsaturated, and may be substituted or unsubstituted. In some embodiments, cycloalkyl substituents are selected from those having from 3 to 12 ring atoms. Illustrative examples of cycloalkyl substituents include, but are not limited to cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like.

Alkoxy substituents are defined by the group —O-alkyl. In some embodiments, the alkoxy group contains from 1 to 12 carbon atoms of a straight, branched, cyclic configuration and combinations thereof attached to the parent structure through an oxygen. Exemplary alkoxy substituents include, but are not limited to, methoxy, ethoxy, propoxy, isopropoxy, cyclopropyloxy and cyclohexyloxy. In some embodiments, the alkoxy is a lower alkoxy (containing one to six carbon atoms). The alkoxy substituent is optionally substituted.

Alkoxycarbonyl substituents include substituents of the formula (alkoxy)(C=O)— attached through the carbonyl carbon. In some embodiments, the alkoxycarbonyl group contain from 1 to 12 carbon atoms, e.g., C(1-12)-alkoxycarbonyl group. In some embodiments, the alkoxycarbonyl is a lower alkoxycarbonyl (containing 1 to 6 carbon atoms). The alkoxycarbonyl may be substituted or unsubstituted.

Acyl substituents include substituents of the formula Rx—C(O)—, where Rx is alkyl, heteroalkyl, alkenyl, alkynyl, cycloalkyl, heterocycloalkyl, aryl, arylalkyl, heteroaryl, and heteroarylalkyl, each as described herein.

Acyloxy substituents include those of the formula Rx(C=O)O—, where Rx is alkyl, heteroalkyl, alkenyl, alkynyl, cycloalkyl, heterocycloalkyl, aryl, arylalkyl, heteroaryl, heteroarylalkyl, each as described herein.

Amino or "amine" substituents include those of the formula —N($R^b$)$_2$, where Rb is hydrogen, alkyl, (halo)alkyl, alkenyl, alkynyl, carbocyclyl, carbocyclylalkyl, aryl, aralkyl, heterocycloalkyl, heterocycloalkylalkyl, heteroaryl heteroarylalkyl, or other substituent described herein. When —N($R_b$)$^2$ has two $R_b$ substituents other than hydrogen, they can be combined with the nitrogen atom to form a 4-, 5-, 6- or 7-membered ring. For example, —N($R_b$)$^2$ is intended to include, for example, pyrrolidinyl and morpholinyl.

Amide or "amido" substituents include those of the formula —C(O)N($R^y$)$_2$ or —NHC(O)$R^y$, where $R^y$ is selected from the group consisting of hydrogen, alkyl, alkenyl, alkynyl, carbocyclyl, carbocyclylalkyl, cycloalkyl, aryl, heteroaryl, or other substituent described herein. The $R^y$ of —N($R^y$)$_2$ of the amide may optionally be taken together with the nitrogen to which it is attached to form a 4-, 5-, 6- or 7-membered ring.

In some embodiments, a substituent is aromatic, meaning that the substituent is an unsaturated, cyclic and planar hydrocarbon group with a delocalized conjugated π system having 4n+2π electrons, wherein n is an integer having a value of 0, 1, 2, 3, and so on. In some embodiments, the aromatic group is an "aryl", which refers to an aromatic radical with six to ten ring atoms. That is, an aryl substituent has at least one ring having a conjugated pi electron system which is carbocyclic. Aryl includes monocyclic or fused-ring polycyclic groups. Aryl may include substituents as described herein, for example, "aralkyl" or "arylalkyl". Aryl includes carbocyclic and heterocyclic ring systems.

An "ester" as used herein refers to a chemical radical of formula —COOR$_2$, where R$_2$ includes, but is not limited to, alkyl, alkenyl, alkynyl, alkyl, alkenyl, alkynyl, cycloalkyl, cycloalkenyl, heterocyclyl, aryl, heteroaryl, aralkyl, and heteraralkyl, or other substituent described herein.

In some embodiments, the substituent is a halogen (e.g., fluoro, chloro, bromo or iodo). Thus, substituents include haloalkyl, haloalkenyl, haloalkynyl and haloalkoxy.

In some embodiments, a substituent is sulfanyl, which refers to substituents that include —S-(optionally substituted alkyl), —S-(optionally substituted aryl), —S-(optionally substituted heteroaryl) and —S-(optionally substituted heterocycloalkyl). In some embodiments, at least one substituent is a sulfinyl, which refers to substituents that include —S(O)—H, —S(O)-(optionally substituted alkyl), —S(O)-(optionally substituted amino), —S(O)-(optionally substituted aryl), —S(O)-(optionally substituted heteroaryl) and —S(O)-(optionally substituted heterocycloalkyl). In some embodiments, at least one substituent is sulfonyl, which refers to substituents that include —S(O$_2$)—H, —S(O$_2$)-(optionally substituted alkyl), —S(O$_2$)-(optionally substituted amino), —S(O$_2$)-(optionally substituted aryl), —S(O$_2$)-(optionally substituted heteroaryl), and —S(O$_2$)-(optionally substituted heterocycloalkyl). In some embodiments, at least one substituent is sulfonamidyl, which refers to a —S(=O)$_2$—NR$_2$ radical. In some embodiments, at least one substituent is sulfoxyl, which refers to a —S(=O)$_{20}$H substituent. In some embodiments, at least one substituent is a sulfonate, which refers to a —S(=O)$_2$—OR radical.

Heteroalkyl, heteroalkenyl, and heteroalkynyl substituents include optionally substituted alkyl, alkenyl and alkynyl radicals and which have one or more skeletal chain atoms selected from an atom other than carbon, e.g., oxygen, nitrogen, sulfur, phosphorus or combinations thereof.

In various embodiments, the present invention contemplates the use of a stilbene or a stilbenoid compound having the general structure:

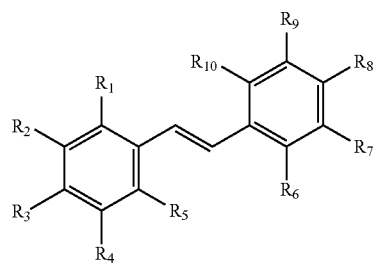

wherein each of R$_1$ to R$_{10}$ can be independently hydrogen or a substituent as defined above. For example, each of R$_1$ to R$_{10}$ can be independently selected from H, hydroxyl, alkyloxy, alkyl, alkenyl, C(O)OH, alkyl ester, amino, amido, aryl, alkylaryl, or halo (e.g., Cl or F) wherein any two adjacent R substituents may form a 5- or 6-membered carbocyclic or heterocyclic ring. In various embodiments, one, two, three, four, or five of R$_1$-R$_{10}$ are not hydrogen.

In some embodiments, the stilbene or stilbenoid compound is resveratrol. Resveratrol is 3,5,4'-trihydroxystilbene and has both cis and trans isomers. The structure of trans-resveratrol is as shown below:

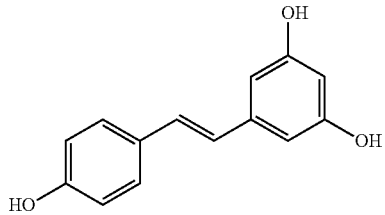 [SMILES: Oc1ccc(/C=C/c2cc(O)cc(O)c2)cc1]

The structure of cis-resveratrol is as shown below:

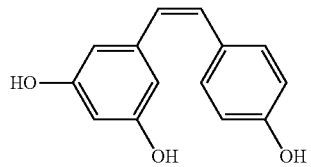 [SMILES: Oc1ccc(/C=C\c2cc(O)cc(O)c2)cc1]

In an embodiment, the compositions and methods of the invention utilize trans-resveratrol.

In some embodiments, the present invention contemplates the use of a prodrug. The term "prodrug" as used herein refers to a compound that is converted under physiological conditions or by solvolysis or metabolically (e.g., in vivo) to a specified compound that is pharmaceutically active. An exemplary resveratrol prodrug is 3,5,4'-tri-O-acetylresveratrol (taRES).

In some embodiments, the present invention contemplates the use of a solvate. The term "solvate" as used herein refers to a pharmaceutically acceptable solvate form of a specified compound that retains the biological effectiveness of such compound. Examples of solvates include a therapeutic compound in combination with, for example, water, isopropanol, ethanol, methanol, DMSO, ethyl acetate, acetic acid, or ethanolamine.

In some embodiments, the present invention contemplates the use of active metabolite. The term "active metabolite" as used herein refers to a pharmacologically active product produced through metabolism in the body of a specified compound. Exemplary resveratrol (and other stilbenoid) metabolites include, for example, glucuronide and sulfate metabolites.

In various embodiments, the stilbene or stilbenoid compound is as described in Pezzuto et al., (2013) *Expert Opin. Ther. Pat.* 23 (12):1529-46, the entire contents of which is hereby incorporated by reference. In certain embodiments, the stilbene or stilbenoid compound has a structural scaffold selected from (where R is a substituent selected from those defined above, and as needed to conform with the laws of chemistry and to form a stable molecule):

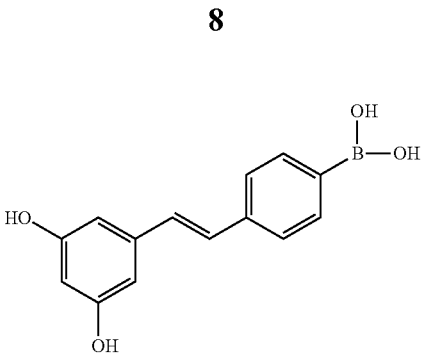

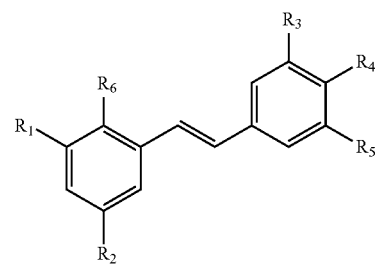

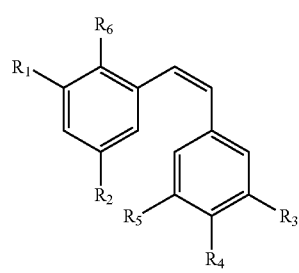

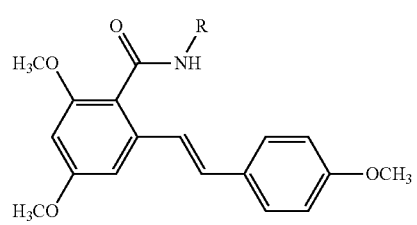

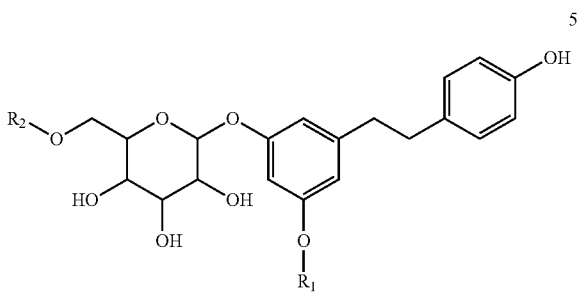

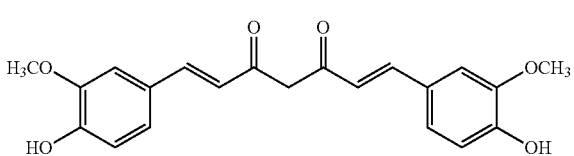

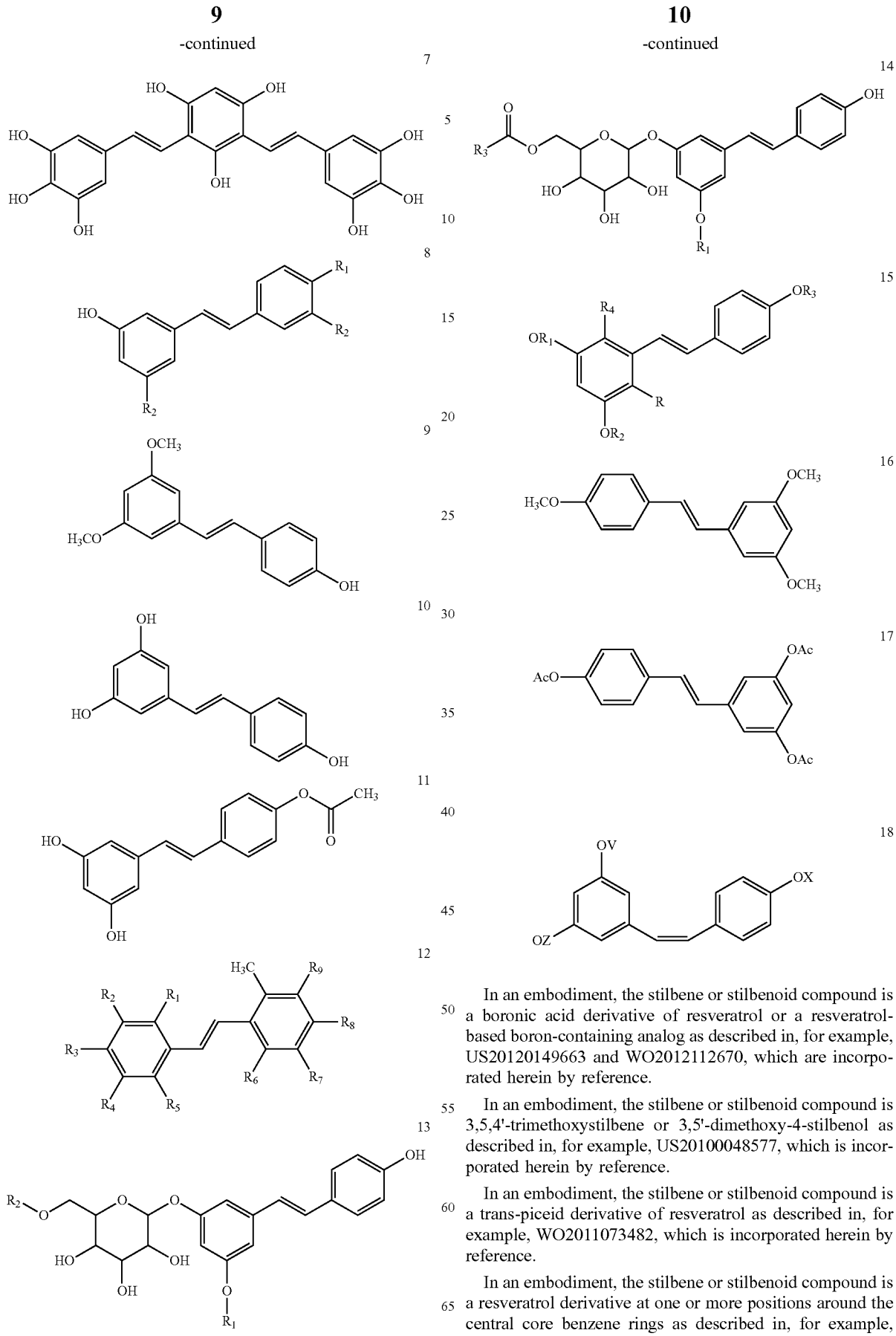

In an embodiment, the stilbene or stilbenoid compound is a boronic acid derivative of resveratrol or a resveratrol-based boron-containing analog as described in, for example, US20120149663 and WO2012112670, which are incorporated herein by reference.

In an embodiment, the stilbene or stilbenoid compound is 3,5,4'-trimethoxystilbene or 3,5'-dimethoxy-4-stilbenol as described in, for example, US20100048577, which is incorporated herein by reference.

In an embodiment, the stilbene or stilbenoid compound is a trans-piceid derivative of resveratrol as described in, for example, WO2011073482, which is incorporated herein by reference.

In an embodiment, the stilbene or stilbenoid compound is a resveratrol derivative at one or more positions around the central core benzene rings as described in, for example, WO2012129499, which is incorporated herein by reference.

In an embodiment, the stilbene or stilbenoid compound is a methylated curcumin-resveratrol hybrid molecule as described in, for example, U.S. Pat. No. 8,350,093, which is incorporated herein by reference.

In an embodiment, the stilbene or stilbenoid compound is pterostilbene or cocrystals thereof as described in, for example, WO2009032870, WO2012154956, and US20110189275, which are incorporated herein by reference.

In an embodiment, the stilbene or stilbenoid compound is 4-acetoxy-resveratrol as described in, for example, WO2011130400, which is incorporated herein by reference.

In an embodiment, the stilbene or stilbenoid compound is a glucopyranoside derivative of resveratrol as described in, for example, WO2011073482, which is incorporated herein by reference.

In an embodiment, the stilbene or stilbenoid compound includes resveratrol with alkyl, prenyl or geranyl additions as described in, for example, WO2009012910, which is incorporated herein by reference.

In an embodiment, the stilbene or stilbenoid compound is a methoxy and/or acetyl derivative of resveratrol in a β-cyclodextrin complex as described in, for example, WO2009012551 and US20130040921, which are incorporated herein by reference.

Additional stilbene or stilbenoid compound and/or compositions comprising the same that may be used in accordance with the invention include those described in, for example, US20100183524, US20130035305, WO2010004256, US20120178801, US20090326000, US20100310615, US20120165280, WO2009061787, US20120058088, WO2012156275, all of which are incorporated herein by reference.

In an embodiment, the stilbene or stilbenoid compound is piceatannol (designated CTI-101), having the structure of:

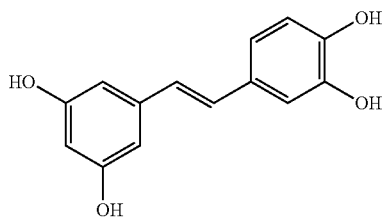 [SMILES: Oc1cc(O)cc(/C=C/c2ccc(O)c(O)c2)c1]

In an embodiment the stilbene or stilbenoid compound has the structure (designated CTI-110):

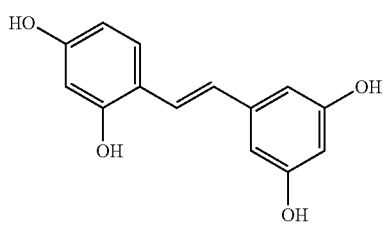 [SMILES: Oc1cc(O)cc(/C=C/c2ccc(O)cc2O)c1]

In an embodiment, the stilbene or stilbenoid compound is 4,4'-stilbenedicarboxylic acid (designated CTI-111) having the structure of:

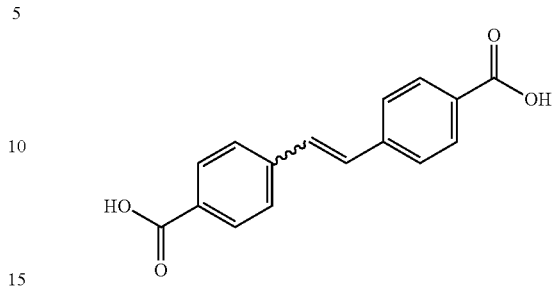

In an embodiment, the stilbene or stilbenoid compound has the structure (designated CTI-112):

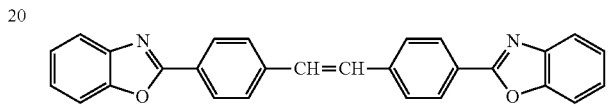

In an embodiment, the stilbene or stilbenoid compound has the structure (designated CTI-113):

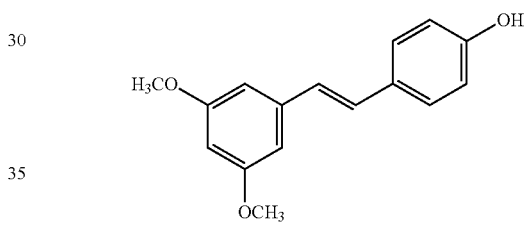

In various embodiments, the compound is capable of crossing the blood-brain barrier. In some embodiments, the compound is a hydroxylated or carboxylated stilbene, and/or is not charged at physiological pH.

In some embodiments, a stilbenoid compound is selected that has reduced metabolism in the liver (as compared to resveratrol). See Setoguchi et al., *Absorption and metabolism of piceatannol in rats*, J Agric Food Chem. 62 (12): 2541-8 (2014); Roupe K A, et al., *Pharmacokinetics of selected stilbenes: rhapontigenin, piceatannol and pinosylvin in rats*, J. Pharm. Pharmacol. 58 (11):1443-50 (2006). In still other embodiments, the stilbenoid is selected so as to accumulate in selected tissues or organs.

In various embodiments, the present invention provides pharmaceutical compositions comprising the stilbene or stilbenoid compound, and a pharmaceutically acceptable carrier or excipient as described herein. Exemplary excipients include sodium citrate, dicalcium phosphate, etc., and/or a) fillers or extenders such as starches, lactose, sucrose, glucose, mannitol, silicic acid, microcrystalline cellulose, and Bakers Special Sugar, etc., b) binders such as, for example, carboxymethylcellulose, alginates, gelatin, polyvinylpyrrolidone, sucrose, acacia, polyvinyl alcohol, polyvinylpolypyrrolidone, methylcellulose, hydroxypropyl cellulose (HPC), and hydroxymethyl cellulose etc., c) humectants such as glycerol, etc., d) disintegrating agents such as agar-agar, calcium carbonate, potato or tapioca starch, alginic acid, certain silicates, sodium carbonate, cross-linked polymers such as crospovidone (cross-linked polyvinylpyrrolidone), croscarmellose sodium (cross-linked sodium carboxymethylcellulose), sodium starch glycolate, etc., e) solution retarding agents such as paraffin, etc., f) absorption accelerators such as quaternary ammonium compounds, etc., g) wetting agents such as, for example, cetyl alcohol and glycerol monostearate, etc., h) absorbents such as kaolin and bentonite clay, etc., and i) lubricants such as talc, calcium stearate, magnesium stearate, solid polyethylene glycols, sodium lauryl sulfate, glyceryl behenate, etc., and mixtures of such excipients. One of skill in the art will recognize that particular excipients may have two or more functions in the oral dosage form.

Pharmaceutical compositions of the present invention may be administered by any route which is compatible with the particular compound or pharmaceutically composition. It is contemplated that the compositions of the present invention may be provided to a subject by any suitable means, directly (e.g., locally, as by injection, implantation or topical administration to a tissue) or systemically (e.g., parenterally or orally). In an embodiment, the pharmaceutical composition is administered orally. In another embodiment, the pharmaceutical composition is administered parenterally. In an embodiment, the pharmaceutical composition is administered by intravenous injection.

In various embodiments, the pharmaceutical composition described herein is formulated as a composition adapted for a mode of administration described herein. For example, the pharmaceutical composition can take the form of solutions, suspensions, emulsion, drops, tablets, pills, pellets, capsules, capsules containing liquids, gelatin capsules, powders, suppositories, emulsions, aerosols, sprays, suspensions, lyophilized powder, frozen suspension, dessicated powder, delayed-release formulations, sustained-release formulations, controlled-release compositions, nanoparticle formulations, or any other form suitable for use.

In certain embodiments, the pharmaceutical composition is formulated for oral administration. Pharmaceutical compositions for oral delivery can be in the form of tablets, lozenges, aqueous or oily suspensions, granules, powders, sprinkles, emulsions, capsules, syrups, or elixirs, for example. Orally administered pharmaceutical compositions can additional comprise, for example, sweetening agents such as fructose, aspartame or saccharin; flavoring agents such as peppermint, oil of wintergreen, or cherry; coloring agents; and preserving agents, to provide a pharmaceutically palatable preparation. In one embodiment, the pharmaceutical composition is in the form of a capsule. In another embodiment, the pharmaceutical composition is in the form of a tablet. In yet another embodiment, the pharmaceutical composition is formulated in the form of a soft-gel capsule. In a further embodiment, the pharmaceutical composition is formulated in the form of a gelatin capsule. In another embodiment, the pharmaceutical composition is formulated as a nanoparticle formulation. In yet another embodiment, the pharmaceutical composition is formulated as a liquid.

In certain embodiments, the pharmaceutical composition is formulated for parenteral administration. Pharmaceutical compositions for parenteral delivery include, for example, solutions, suspensions, dispersions, emulsions, and the like. They may also be manufactured in the form of sterile solid compositions, which can be dissolved or suspended in sterile injectable medium immediately before use. Pharmaceutical compositions for parenteral delivery may contain, for example, suspending or dispersing agents known in the art. Exemplary suspending agents include, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof. Additional components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose.

The formulations comprising the therapeutic agents of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

It will be appreciated that the actual dose of the therapeutic agent to be administered according to the present invention will vary according to the particular compound, the particular dosage form, and the mode of administration. Many factors that may modify the action of the therapeutic agent (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose.

The desired dose of the therapeutic agent may be presented as one dose or two or more sub-doses administered at appropriate intervals throughout the dosing period (e.g., one hour, one day, one week etc). Exemplary daily doses of the stilbene or stilbenoid compound are in the range of about 10 mg to about 5,000 mg, or from about 10 mg to about 2,500 mg, from about 10 mg to about 1,000 mg, from about 10 mg to about 500 mg, or from about 10 mg to about 250 mg, or from about 10 mg to about 100 mg active ingredient per unit dosage form. In some embodiments, the daily dose is within the range of 100 mg to 1000 mg, or is about 200 mg to about 1000 mg, or is about 300 mg to about 1000 mg, or is about 400 mg to about 1000 mg, or is about 500 mg to about 1000 mg. Exemplary daily doses are about 10 mg, about 15 mg, about 20 mg, about 25 mg, about 30 mg, about 40 mg, about 50 mg, about 60 mg, about 70 mg, about 75 mg about 80 mg, about 90 mg, about 100 mg, about 125 mg, about 150 mg, about 175 mg, about 200 mg, about 225 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 2000 mg, about 3000 mg, about 4000 mg, about 5000 mg, inclusive of all values and ranges therebetween. As used herein, the term "about" means + or − 10% of the recited value.

In accordance with certain embodiments of the invention, the pharmaceutical composition of the invention may be administered, for example, more than once daily, about once per day, about every other day, about every third day, about once a week, about once every two weeks, about once every month. In an embodiment, the pharmaceutical composition is administered more than once daily, for example, twice, three times, four times, five times, or six times daily. In another embodiment, the pharmaceutical composition is administered once daily. In some embodiments, the regimen is continued for at least one month, at least six months, at least nine months, or at least one year. In various embodiments, the pharmaceutical compositions are administered from 1 to 3 times daily.

In various embodiments, the pharmaceutical composition of the invention may be administered with meals, beverages, or food, which in some embodiments, enhances the bioavailability of and/or is synergistic with treatment with the stilbene or stilbenoid compound as described herein. In an embodiment, the pharmaceutical composition is administered together with meals. In an embodiment, the pharmaceutical composition is administered together with a beverage, such as grape juice, tomato juice, or red wine. In an embodiment, the pharmaceutical composition is administered together with a polyphenol. Exemplary polyphenols include, for example, piperine and quercetin. In an embodiment, the pharmaceutical composition is administered together with curcumin.

Pharmaceutical compositions of the invention may be administered to a subject in combination with an additional therapy, which in some embodiment, is synergistic with treatment with the stilbene or stilbenoid compound as described herein. In an embodiment, the pharmaceutical composition of the invention is administered to a subject who has undergone, is undergoing, or will undergo enzyme replacement therapy (ERT). Exemplary ERT includes, for example, Aldurazyme (for the treatment of MPS I), Elaprase (for the treatment of MPS II), Vimizim™ (for the treatment of MPS IVA), and Naglazyme (for the treatment of MPS VI). In another embodiment, the pharmaceutical composition of the invention is administered to a subject who has undergone, is undergoing, or will undergo bone marrow transplantation (BMT). In a further embodiment, the pharmaceutical composition of the invention is administered to a subject who has undergone, is undergoing, or will undergo umbilical cord blood transplantation (UCBT).

In still other embodiments, the compositions described herein are administered as an alternative to enzyme replacement therapy, or allow for lower doses or less frequent ERT to be delivered.

EXAMPLES

Example 1. Administration of Resveratrol Restores IDUA Expression and/or Activity A cell culture experiment was performed in MPS-I patient-derived fibroblast cells. Cells were cultured overnight in a 384-well plate, at a concentration of 20,000 cells per well in advanced DMEM media (Life Technologies) supplemented with 15% FBS (Life technologies), 1× Glutamax (Life Technologies) and beta-mercaptoethanol (1:125000 dilution). The next day, cells were treated with the indicated compound with final concentrations including, but not limited to: 100 µM, 30 µM, 10 µM, 3.3 µM, 1.1 µM, 0.37 µM and 0.12 µM depending on experiment. Treated cells were then incubated for 48 hours at 37° C., 5% $CO_2$, 95% humidity. Cells were then washed with HBSS buffer, and 25 µM of the fluorogenic substrate 4-Methylumbelliferyl α-L-iduronide (free acid) (Santa Cruz Biotechnology) were added in the presence of 0.2M $CHNaO_2$, 0.1% BSA, and 0.1% Triton X. After the addition of the 4-Methylumbelliferyl α-L-iduronide substrate, cells were incubated at 37° C. for 3 to 4 hours, placed at room temperature for 30 minutes to stabilize and alpha-L-iduronidase (IDUA) enzyme activity was measured using the EnVision Multilabel Plate Reader (Perkin Elmer, Inc.). Compounds were purchased from Tocris, Cayman Chemicals or Sigma-Aldrich.

An increase in IDUA enzyme activity was observed with many of the compounds tested (FIG. 1). Compounds tested include CTI-101, CTI-102, CTI-111, CTI-110, CTI-112, and CTI-113, whose structures are shown herein. Buffer only control represents patient cells with no stilbene or stilbenoid compound.

Several compounds were tested that did not show an increase in alpha-L-iduronidase activity, including:

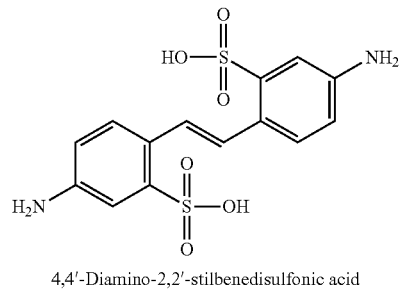

4,4'-Diamino-2,2'-stilbenedisulfonic acid

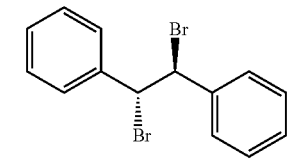

Meso-1,2-Dibromo-1,2-diphenylethane

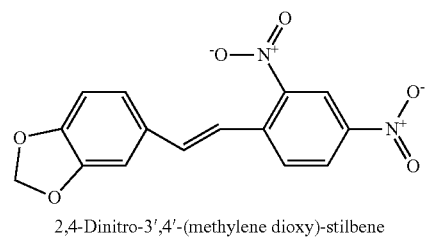

2,4-Dinitro-3',4'-(methylene dioxy)-stilbene

Figure 3:
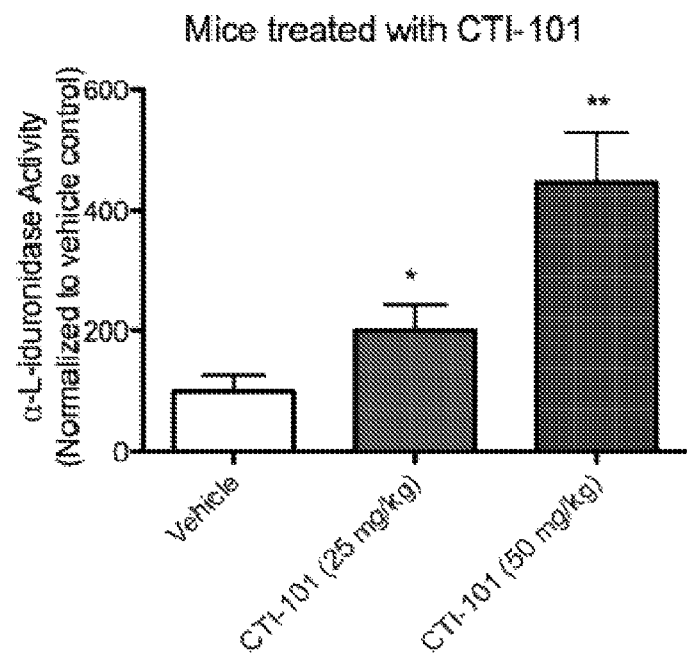
FIG. 3 shows the elevation of α-iduronidase activity in plasma of mice treated with piceatannol (top) or resveratrol (bottom) for one month. At 50 mg/kg/day, both resveratrol and piceatannol provided substantial boosts in enzyme activity.
Figure 3:
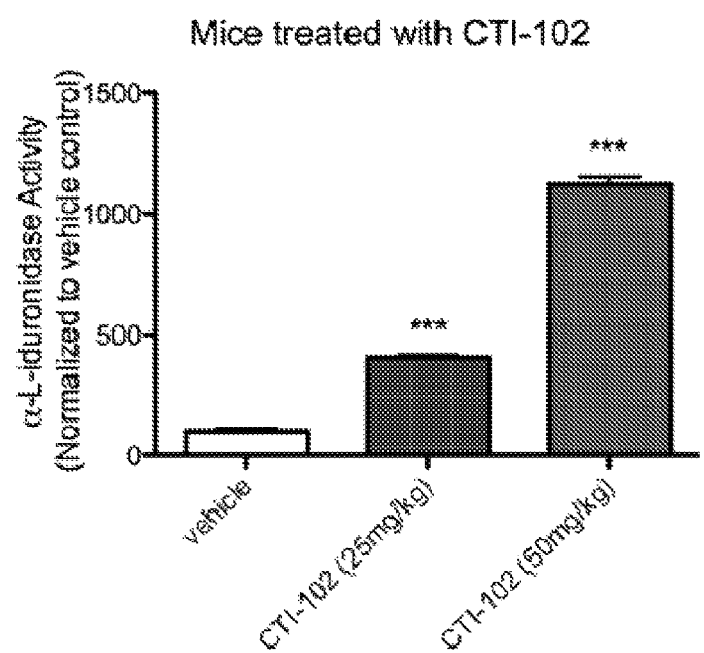

Increases in alpha-L-iduronidase activity were also observed in the plasma of mice treated with either 25 mg/kg or 50 mg/kg daily of CTI-101 or CTI-102 for a duration of 1 month. See FIG. 3.

Figure 2:
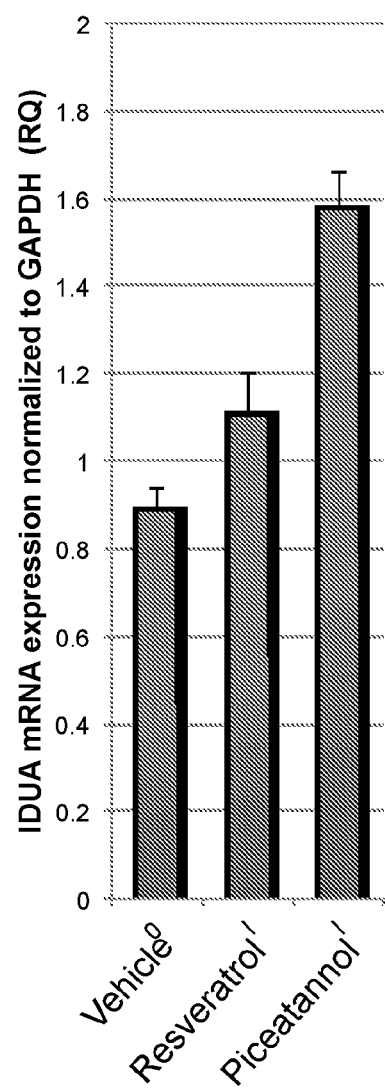
FIG. 2 shows that treatment of MPS I patient cells with resveratrol and piceatannol increased the mRNA level of α-L-iduronidase (IDUA).

Tests were subsequently conducted to determine whether the increase in activity could in-part be attributed to increases in gene expression. As shown in FIG. 2 both resveratrol and Piceatannol showed an increase in IDUA mRNA expression in patient cells (normalized to GAPDH). Resveratrol and Piceatannol were added to patient cells for 48 hours, in the same conditions mentioned above.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

INCORPORATION BY REFERENCE

All patents and publications referenced herein are hereby incorporated by reference in their entireties.

The invention claimed is:

1. A method of treating mucopolysaccharidosis I (MPS-I) in a subject in need thereof, comprising administering to the subject a therapeutically effective amount of a pharmaceutical composition comprising trans-resveratrol or a pharmaceutically acceptable salt, ester, or prodrug thereof, wherein the composition increases plasma alpha-L-iduronidase activity in vivo, and wherein the effective amount is from 25 to 50 mg/kg daily.

2. The method of claim 1, wherein the MPS-I is Scheie syndrome (MPS I-S).

3. The method of claim 1, wherein the MPS-I is Hurler-Scheie syndrome (MPS I-H/S).

4. The method of claim 1, wherein the trans-resveratrol or pharmaceutically acceptable salt, ester, or prodrug thereof is trans-resveratrol

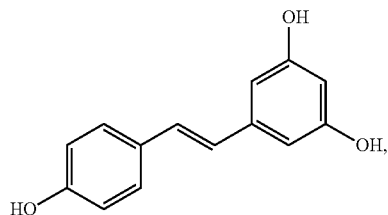 [SMILES: Oc1ccc(/C=C/c2cc(O)cc(O)c2)cc1]

or a pharmaceutically acceptable salt thereof.

5. The method of claim 1, wherein the pharmaceutical composition is formulated for oral administration.

6. The method of claim 5, wherein the pharmaceutical composition is formulated as a capsule or a tablet.

7. The method of claim 5, wherein the pharmaceutical composition is formulated as a liquid.

8. The method of claim 1, wherein the pharmaceutical composition is formulated for parenteral administration.

9. The method of claim 8, wherein the pharmaceutical composition is formulated for intravenous injection.

10. The method of claim 1, wherein the trans-resveratrol or pharmaceutically acceptable salt, ester, or prodrug thereof can cross the blood-brain barrier.

11. The method of claim 1, wherein the pharmaceutical composition is administered at least once daily.

12. The method of claim 1, wherein the prodrug is 3,5,4'-tri-O-acetylresveratrol (taRES).

13. The method of claim 1, further comprising administering to the subject enzyme replacement therapy for the treatment of MPS-I.

* * * * *